US005300641A

United States Patent [19]

Dinh et al.

[11] Patent Number: 5,300,641
[45] Date of Patent: Apr. 5, 1994

[54] PALLADIUM BLACK CATALYZED PROCESS FOR PREPARATION OF (PIPERAZINYLORGANO) SILANES

[75] Inventors: Paul C. Dinh; Peter Y. K. Lo, both of Midland, Mich.

[73] Assignee: Dow Corning Corporation, Midland, Mich.

[21] Appl. No.: 1,964

[22] Filed: Jan. 8, 1993

[51] Int. Cl.$^5$ .................................................. C07F 7/10
[52] U.S. Cl. ...................... 544/229; 556/413; 556/423; 556/424
[58] Field of Search ................ 544/229; 556/413, 424, 556/423

[56] References Cited

U.S. PATENT DOCUMENTS

| | | | |
|---|---|---|---|
| 2,971,864 | 2/1961 | Speier | 556/424 |
| 3,046,295 | 7/1962 | Lisanke et al. | 556/424 |
| 4,028,343 | 6/1977 | Amort et al. | 544/229 |
| 4,526,996 | 7/1985 | Kilgour et al. | 544/358 |
| 4,888,436 | 12/1989 | Shiozawa et al. | 556/413 |

FOREIGN PATENT DOCUMENTS 688662  6/1964  Canada .................. 556/413

OTHER PUBLICATIONS

Thames et al., *J. Chem. Soc.,* p. 2339 (1968).
Lukevits et al. Zhurnal obshchei Khimii 50 (2):388-389 (1980).

*Primary Examiner*—Emily Bernhardt
*Attorney, Agent, or Firm*—William F. Boley

[57] ABSTRACT

The present invention is a process for the preparation of (piperazinylorgano)silanes. The process involves the contact of an (aminoorgano)silane with piperazine or an organopiperazine, in the presence of palladium black as a catalyst. The process is run at a temperature within a range of about 50° C. to 300° C. in a standard low-pressure type reactor.

11 Claims, No Drawings

PALLADIUM BLACK CATALYZED PROCESS FOR PREPARATION OF (PIPERAZINYLORGANO) SILANES

BACKGROUND OF INVENTION

The present invention is a process for the preparation of (piperazinylorgano)silanes. The process involves the contact of an (aminoorgano)silane with piperazine or an organopiperazine, in the presence of palladium black as a catalyst.

Lisanke et al., U.S. Pat. No. 3,046,295. issued Jul. 24, 1962, teaches that (cyanoalkyl)silanes can react with a diamine, such as ethylene diamine, in the presence of a nickel catalyst and hydrogen to form N-(aminoalkyl-)aminoalkylsilanes. The process requires elevated pressures to run.

Lukevits et al., Zhurnal Obshchei Khimii 50(2):388-389 (1980), describes two processes for the preparation of (piperazinylalkyl)silanes. The first process involves heating a trialkyl(chloroalkyl)silane with a 1-organopiperazine in the presence of a threefold excess of toluene and in the presence of potassium carbonate. The second process involves the addition of trialkylvinylsilane to organopiperazine in the presence of lithium.

The object of the present invention is to provide a process where palladium black is a catalyst for the reaction of an (aminoorgano)silane with piperazine or an organopiperazine. The present process offers advantages over the cited art in that no elevate pressure is required or chloride salts formed. In addition, there is no need for additives such as lithium or potassium carbonate.

SUMMARY OF INVENTION

The present invention is a process for the preparation of (piperazinylorgano)silanes. The process involves the contact of an (aminoorgano)silane with piperazine or an organopiperazine, in the presence of palladium black as a catalyst. The process is run at a temperature within a range of about 50° C. to 300° C. in a standard low-pressure type reactor.

DESCRIPTION OF INVENTION

The present invention is a process for the preparation of (piperazinylorgano)silanes. The process comprises:
(A) contacting an (aminoorgano)silane of formula

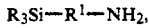

$$R_3Si-R^1-NH_2, \quad (1)$$

a piperazine of formula

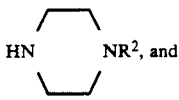

palladium black, at a temperature within a range of about 50° C. to 300° C., and
(B) recovering a (piperazinylorgano)silane of formula

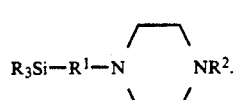

For the described process, each R is independently selected from a group consisting of alkyl radicals of 1 to 20 carbon atoms, cycloalkyl radicals of 3 to 20 carbon atoms, aryl radicals, and alkoxy radicals of formula $R^3O-$, where $R^3$ is an alkyl radical of 1 to 20 carbon atoms; $R^1$ is selected from a group consisting of divalent hydrocarbon radicals of 1 to 20 carbon atoms and divalent polyethers containing 2 to 20 carbon atoms; and $R^2$ is selected from a group consisting of alkyl radicals of 1 to 20 carbon atoms, cycloalkyl radicals of 3 to 20 carbon atoms, aryl radicals, and hydrogen.

Contacting the (aminoorgano)silane, the piperazine, and the palladium black can be conducted in any standard reactor for effecting contact between liquids and solids. The reactor can be, for example, a fixed-bed, a stirred-bed, or a fluidized-bed reactor. The process can be run as a batch process, semi-continuous process, or a continuous process. Preferred is when the present process is run as a batch process in a stirred-bed reactor.

When the present process is run as a batch process, it is preferred that a mixture of palladium black and (aminoorgano)silane be formed and the piperazine be added at a controlled rate to this mixture. By "controlled rate" it is meant that the piperazine is added at a rate to avoid significant localized concentration build-ups of the piperazine within the mixture.

When the process is run as a batch process, it is preferred that the final mole ratio of the piperazine to the (aminoorgano)silane be within a range of about 0.5 to 5.0. More preferred is when the mole ratio is within a range of about 1.0 to 3.0. When the present process is run as a semi-continuous process or continuous process, the rate of feed of the piperazine and (aminoorgano)silane can be controlled to provided comparable mole ratios. Alternatively a mixture of the piperazine and (aminoorgano)silane of comparable mole ratios can be formed and fed to the process.

The time required for the (aminoorgano)silane, the piperazine, and palladium black to be contacted to form (piperazinylorgano)silanes will depend upon the catalyst concentration, the reactor temperature, and the specific (aminoorgano)silane being reacted. In general, contact times of five minutes to 20 hours are considered useful when the process is run as a batch process. A preferred contact time for the batch process is within a range of about 15 minutes to one hour. Shorter contact times may be used but may make the process difficult to control and may result in reduced formation of the desired product. When the process is run as a continuous process, contact times of 0.2 minutes to two hours are considered useful. A preferred contact time, for the continuous process, is five minutes to 30 minutes.

For purposes herein, "contact time" is defined as the period beginning when an (aminoorgano)silane molecule, a piperazine molecule, and palladium black are available in a mixture for contact and ending when one of the three are removed from the mixture or the process temperature is lowered below 50° C.

The (aminoorgano)silanes which are useful in the present process are described by Formula (1). The (aminoorgano)silane has three substituents, R, where each R is independently selected from a group consisting of alkyl radicals of 1 to 20 carbon atoms cycloalkyl radicals of 3 to 20 carbon atoms, aryl radicals, and alkoxy radicals of formula $R^3O-$, where $R^3$ is an alkyl radical of 1 to 20 carbon atoms. The radical, R, can be, for example, methyl, ethyl, propyl, isopropyl, butyl, tert-butyl, isobutyl, pentyl, dodecyl, cyclopentyl, cyclohexyl, phenyl, tolyl, xylyl, methoxy, and ethoxy. Preferred is when R is the methoxy radical. The radical, $R^3$ can be, for example, methyl, ethyl, tert-butyl, and isobutyl. Preferred is when $R^3$ is the methyl radical.

The (aminoorgano)silane, described by Formula (1) has substituent $R^1$, where $R^1$ is selected from a group consisting of divalent hydrocarbon radicals of 1 to 20 carbon atoms and divalent polyethers containing 2 to 20 carbon atoms. The radical, $R^1$, can be, for example, alkylenes e.g. methylene, ethylene, propylene, ethylidene, and isopropylidene; cycloalkylenes e.g. cycloheptylene and cyclohexylene; divalent aromatic compounds e.g. phenylene, tolylene, xylylene, and naphthylene; and divalent radicals of aralkanes of formula $-C_6H_4-R^4$, where $R^4$ is an alkylene radical of less than 20 carbon atoms e.g. methylene, ethylene, or propylene. $R^1$ can be, for example, a polyether of formula $R^5(OR^5)_z$, where $R^5$ is an alkylene of less than 20 carbon atoms and z is an integer of 1 to 5. The divalent polyether radical can be, for example diethylene ether.

Examples of (aminoorgano)silanes useful in the present process are: $(CH_3)_3Si(CH_2)_3NH_2$, $(CH_3O)_3Si(CH_2)_3NH_2$, $(CH_3O)_3Si(CH_2)_2NH_2$, $(CH_3O)_2CH_3Si(CH_2)_3NH_2$, $(CH_3O)_3Si(CH_2)_2O(CH_2)_2NH_2$, $(CH_3CH_2O)_3Si(CH_2)_3NH_2$, $(CH_3)_2C_6H_5Si(CH_2)_3NH_2$, and $(CH_3)_2(C_5H_9)Si(CH_2)_3NH_2$.

The piperazines useful in the present process are described by Formula 2. The piperazine has substituent $R^2$, where $R^2$ is selected from a group consisting of alkyl radicals of 1 to 20 carbon atoms, cycloalkyl radicals of 3 to 20 carbon atoms, aryl radicals, and hydrogen. Examples of the alkyl, cycloalkyl, and aryl radicals are as previously described for R. Preferred is when the piperazine is selected from the group consisting of piperazine and 1-methylpiperazine.

The catalyst for the present process comprises palladium black. By "palladium black" it is meant a finely divided palladium catalyst prepared by the reduction of palladium compounds. The palladium black may be prepared by, for example, the reduction of organometallic palladium compounds. The palladium black may be formed by, for example, the reduction of organometallic palladium compounds such as $\{PdCl(C_3H_5)\}_2$, $\{Pd(C_3H_5)(C_5H_5)\}$ and $\{Pd_2(C_3H_5)(C_5H_5)(PPh_3)_2\}$ by sodium borohydride or hydrazine hydrate. The palladium black may be formed by, for example, the reduction of inorganic compounds of palladium such as palladium halides. The palladium halide can be, for example, $PdCl_2$ and $H_2PdCl_4$. Preferred is a form of palladium black available as palladium black from Aldrich Chemical Co., Inc., Milwaukee, Wis.

A useful concentration of palladium black catalyst is within a range of about 0.1 to 5.0 g of catalyst per mole of (aminoorgano)silane initially present in the reactor. Preferred is when the catalyst is present in a range of about 1.0 to 5.0 g of catalyst per mole of (aminoorgano)silane initially present in the reactor. When the process is run as a semi-continuous process or a continuous process flow of the (aminoorgano)silane can be controlled to maintain these proportions of catalyst to initial (aminoorgano)silane concentration.

A useful temperature for running the present process is within a range of about 50° C. to 300° C. Preferred, is when the temperature is about 180° C. to 250° C. Most preferred is when the process is conducted at the reflux temperature of the liquid mixture resulting from the contact of the (aminoorgano)silane, the piperazine, and the palladium black.

The (piperazinylorgano)silanes which can be prepared by the present process are described by Formula 3, where R, $R^1$, and $R^2$ are as previously described. The (piperazinylorgano)silane can be, for example:

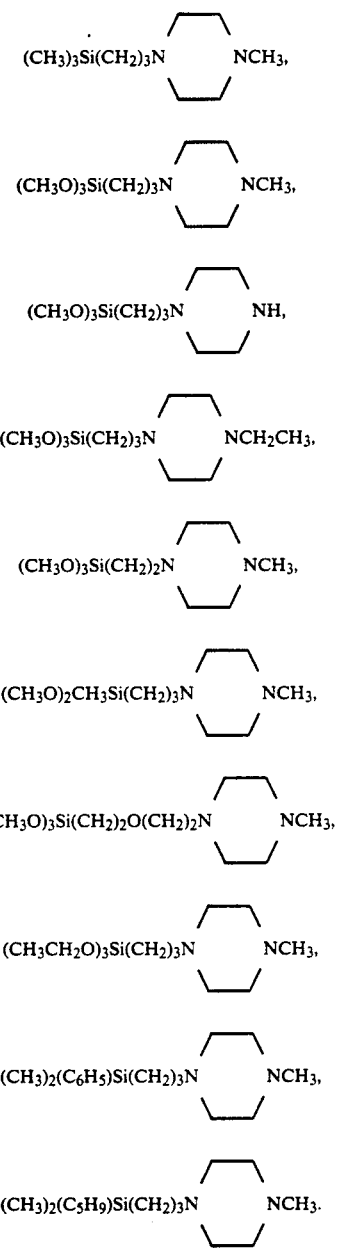

The desired product (piperazinylorgano)silanes can be recovered by standard separation methods for example, filtration and distillation. When the process is run as a batch process, the separated palladium black may be reused in the process.

In order that those skilled in the art may better understand how the present invention may be practiced, the following example is given. This example is given for illustration only and is not meant to limit the present claims.

EXAMPLE 1

1-Methylpiperazine was added to a reactor containing a mixture comprising (aminopropyl)trimethoxysilane and palladium black catalyst. The reactor consisted of a 500 ml 3-neck flask equipped with a reflux condenser, an addition funnel, a magnetic stirring bar, and a thermometer. Approximately 66.9 g of (aminopropyl)trimethoxysilane and 1.0 g of palladium black catalyst (Aldrich Chemical Co., Inc., Milwaukee, Wis.) were added to the reactor. The resultant mixture was stirred and heated to a reflux temperature of about 216° C. Then, about 72.2 g of 1-methylpiperazine was added dropwise over a six hour period, from the addition funnel. The temperature was kept at reflux during the course of addition of the 1-methylpiperazine, resulting in a final temperature of about 145° C. After completion of the addition of the 1-methylpiperazine, the resultant mixture was kept at about 145° C. for an additional two hours. The mixture was then cooled and analyzed as described for Example 1. The GC-MS trace showed 2.5 area percent ((4-methyl-1-piperazinyl)propyl)trimethoxysilane, 61.8 area percent 1-methylpiperazine, 1.4 area percent 1-(aminopropyl)trimethoxysilane, 12.6 area percent bis-(3-trimethyoxysilylpropyl)amine, and 12.6 area percent of unidentified high boiling compounds.

We claim:

1. A process for preparation of (piperazinylorgano)silanes, the process comprising:

(A) contacting an (aminoorgano)silane selected from a group consisting of $(CH_3)_3Si(CH_2)_3NH_2$, $(CH_3O)_3Si(CH_2)_3NH_2$, $(CH_3O)_3Si(CH_2)_2NH_2$, $(CH_3O)_2CH_3Si(CH_2)_3NH_2$, $(CH_3O)_3Si(CH_2)_2O(CH_2)_2NH_2$, $(CH_3CH_2O)_3Si(CH_2)_3NH_2$, $(CH_3)_2C_6H_5Si(CH_2)_3NH_2$, and $(CH_3)_2(C_5H_9)Si(CH_2)_3NH_2$, a piperazine compound selected from a group consisting of piperazine and 1-methylpiperazine, and palladium black, at a temperature within a range of about 180° C. to 250° C., where the final mole ratio of the piperazine compound to the (aminoorgano)silane is within a range of about 1.0 to 3.0; and (B) recovering (piperazinylorgano)silane product.

2. A process according to claim 1, where the process is run as a batch process in a stirred-bed reactor.

3. A process according to claim 1, where the process is run as a batch process and contact of the (aminoorgano)silane, the piperazine compound, and the palladium black is for a time of about five minutes to 20 hours.

4. A process according to claim 1, where the process is run as a batch process and contact of the (aminoorgano)silane, the piperazine compound, and the palladium black is for a time of about 25 minutes to one hour.

5. A process according to claim 1, where the process is run as a continuous process and contact of the (aminoorgano)silane, the piperazine compound, and the palladium black is for a time of about 0.2 minute to two hours.

6. A process according to claim 1, where the process is run as a continuous process and contact of the (aminoorgano)silane, the piperazine compound, and the palladium black is for a time of about five minutes to 30 minutes.

7. A process according to claim 1, where the (aminoorgano)silane is (aminopropyl)trimethoxysilane.

8. A process according to claim 1, where concentration of the palladium black is about 0.1 g to 5.0 g per mole of (aminoorgano)silane initially present.

9. A process according to claim 1, where the (piperazinylorgano)silane product is ((4-methyl-1-piperazinyl)propyl)trimethoxysilane.

10. A process according to claim 1, where the palladium black is formed by the reduction of an organometallic palladium compound.

11. A process according to claim 1, where the palladium black is formed by the reduction of a palladium halide.

* * * * *